United States Patent [19]
Son

[11] 4,006,140
[45] Feb. 1, 1977

[54] MORPHOLINOTHIO OXAMIDES

[75] Inventor: Pyong-Nae Son, Akron, Ohio

[73] Assignee: The B. F. Goodrich Company, Akron, Ohio

[22] Filed: June 19, 1975

[21] Appl. No.: 588,310

Related U.S. Application Data

[62] Division of Ser. No. 367,642, June 6, 1973, Pat. No. 3,910,864.

[52] U.S. Cl. .................... 260/246 B; 260/247.1 L; 260/247.1 M
[51] Int. Cl.² .................................... C07D 295/22
[58] Field of Search ............... 260/247.1 R, 246 B

[56] References Cited

UNITED STATES PATENTS 3,234,275  2/1966  Malz et al. ................. 260/247.1 R

OTHER PUBLICATIONS

Son, "Chem. Abstracts" vol. 82, (1975) No. 141, 394m.

*Primary Examiner*—Natalie Trousof
*Assistant Examiner*—R. W. Ramsuer
*Attorney, Agent, or Firm*—Alan A. Csontos

[57] ABSTRACT

Vulcanizable rubber compositions comprising a sulfur vulcanizable rubber, sulfur, a thiazole sulfenamide accelerator, a morpholinothio amide compound, and optionally a benzothiazole or thiuram accelerator exhibit good scorch safety and yield vulcanizates having excellent original and heat aged properties.

3 Claims, No Drawings

MORPHOLINOTHIO OXAMIDES

This is a division of application Ser. No. 367,642, filed June 6, 1973, and now U.S. Pat. No. 3,910,864.

BACKGROUND OF THE INVENTION

It is known in the art that the use of various specific sulfur-accelerator combinations yield rubber vulanizates having particularly desirable properties. One instance of this is the use of sulfur and 2-benzothiazole 4-morpholine disulfide (BMD) to yield vulcanizates having excellent thermal aged properties. Such vulcanizates would be extremely useful as gaskets, automotive hose and tires, and other products where good retention of properties on heat aging is needed. Unfortunately, the sulfur-BMD cure system is very fast acting, and yields quite scorchy rubber compositions having little processing safety. This prevents the use of such a cure system in operations where the vulcanizable rubber compositions must be handled and processed for extended periods at elevated temperatures, as in tire manufacturing. The use of known cure retarders provides only a marginal increase in scorch safety when employed with the sulfur-BMD cure system.

SUMMARY OF THE INVENTION

Vulcanizable rubber compositions comprising (1) a sulfur vulcanizable rubber, (2) sulfur, (3) a thiazole sulfenamide accelerator, (4) a morpholinothioamide compound selected from the group consisting of morpholinothiooxamides of the formula

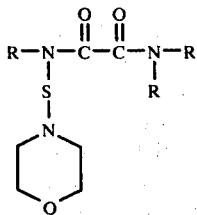

wherein R is selected from the group consisting of hydrogen, alkyl radicals containing 1 to 24 carbon atoms, an aryl, alkaryl, or aralkyl radical containing 6 to 18 carbon atoms, a cycloalkyl radical containing 3 to 8 carbon atoms in the ring, and the group

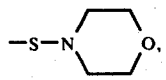

and a morpholinothio cyclic hydrocarbon of the formula

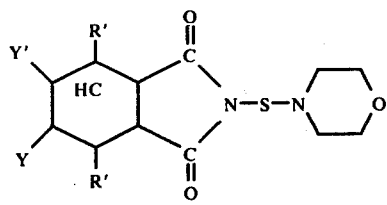

wherein R' is hydrogen or an alkyl radical containing 1 to 4 carbon atoms and Y and Y' are the same as R', or Y and Y' together with the common carbon atoms on the HC ring form a cyclic hydrocarbon ring or a cyclic imide ring, and optionally (5) a benzothiazole or thiuram accelerator exhibit good scorch safety on curing and yield vulcanizates having excellent original and heat aged properties. Vulcanizate properties are comparable with those obtained using a sulfur-BMD cure system.

DETAILED DESCRIPTION

The vulcanizable rubber compositions comprise (1) a sulfur vulcanizable rubber, (2) sulfur, (3) a thiazole sulfenamide accelerator, (4) a morpholinothioamide compound, and optionally (5) a benzothiazole or thiuram accelerator. The rather complex system represents a unique balance of cure factors which yields good scorch safety at processing temperatures and vulcanizates having excellent original and heat aged properties. The compositions are particularly useful to prepare articles that require relatively long processing and shaping operations and/or are subject to thermal aging conditions. Such articles would be tires, belting, hose, gasketing, seals, and the like.

The sulfur vulcanizable rubber contains from about 0.5 percent to about 50 percent by weight of olefinic ($>C=C<$) unsaturation based upon the weight of the polymer. The olefinic groups can be in the polymer main chain (backbone) or in pendant (side-chain) groups, or both. Examples of such polymers are high unsaturation rubbers such as natural rubber, cis-polyisoprene, cis-polybutadiene (CB), emulsion polybutadiene, butadiene-acrylonitrile (NBR) rubbers, isoprene-acrylonitrile rubbers, polychloroprene, polypentenamer rubbers, butadiene-styrene rubbers (SBR), isoprene-styrene rubbers, and the like; and low unsaturation polymers such as isoprene-isobutylene (butyl) rubbers, copolymers of conjugated dienes with lower alkyl and alkoxy acrylates like ethyl acrylate, butyl acrylate, methoxyethyl acrylate, and the like; polyether, terpolymers containing up to 20 percent by weight of glycidyl acrylate, allyl glycidyl ether, and the like; and ethylene-propylenediene polymers (EPDM) containing from about 0.5 percent to about 20 percent by weight of a diene monomer where the diene can be conjugated as in butadiene, 1,3-pentadiene, and the like; non-conjugated as in 1,4-pentadiene, 1,4-hexadiene, and the like; cyclic dienes as in cyclopentadiene, dicyclopentadiene, and the like; an alkenyl norbornene such as 5-ethylidene-2-norbornene, 2-isopropenyl-5-norbornene, and the like; and others such as 3-ethylbicyclonondiene, methyltetrahydroindene, and 3-methyl-tricyclo-$(5,2,1,0^{2,6})$-3,8-decadiene.

Although the disclosure is directed to the use of a sulfur vulcanizable rubber, blends of two or more sulfur vulcanizable rubbers are readily employed. For example, the rubber can be a polymer blend of styrene-butadiene rubber and polybutadiene rubber, or a terblend of natural or polyisoprene rubber with polybutadiene and poly(butadiene-styrene)rubber.

The second ingredient in the composition is sulfur. The level employed ranges from about 0.1 part to 0.8 part by weight per 100 parts by weight of the sulfur vulcanizable rubber. More preferredly, the level of sulfur is from about 0.2 to about 0.6 part by weight. Excellent results are obtained when the sulfur is used at about 0.5 part by weight per 100 parts of rubber. Use of the sulfur is necessary to achieve the high state of cure and good fatigue life of the composition. However, use of levels of sulfur significantly higher than those designated results in inferior heat aged properties.

The third ingredient is a thiazole sulfenamide compound of the formula T—S—A wherein A is selected from the group consisting of

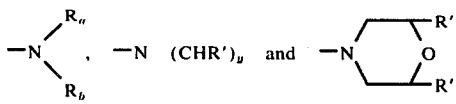

wherein $R_a$ and $R_b$ are hydrogen, alkyl radicals containing 1 to 24 carbon atoms, an aryl radical, alkaryl radical or aralkyl radical containing 6 to 18 carbon atoms, a cycloalkyl radical containing 3 to 8 carbon atoms in the ring, and R' is hydrogen or an alkyl radical containing 1 to 4 carbon atoms and y is 2 to 7; and T is a thiazole ring and especially a benzothiazole ring. The alkyl radicals can be linear or branched and can contain primary, secondary and/or tertiary carbon atom configurations. The aryl, alkaryl, aralkyl, cycloalkyl and thiazole radicals can further be substituted with alkyl radicals containing 1 to 8 carbon atoms.

Examples of the thiazole sulfenamide compounds are N,N-dimethyl-2-benzothiazylsulfenamide, N,N-diisopropyl-2-(4,5-dimethylthiazyl)sulfenamide, N-methyl-N-cyclohexyl-2-(4,5-dimethylthiazylsulfenamide), N,N-diisopropyl-2-benzothiazylsulfenamide, N,N-diethyl-2-benzothiazylsulfenamide, N-methyl-N-benzyl-2-benzothiazylsulfenamide, N,N-di(tert-butyl)-2-benzothiazylsulfenamide, N,N-dicyclohexyl-2-benzothiazylsulfenamide, N-pentamethylene-2-benzothiazylsulfenamide, N-oxydiethylene-2-benzothiazylsulfenamide, N-(2,6-dimethyl)-oxydiethylene-2-benzothiazylsulfenamide, N,N-dimethyl-2-(4,6-dimethylbenzothiazyl)sulfenamide, and the like.

More preferredly, the thiazole sulfenamide is a benzothiazole sulfenamide of the formula

where $T_1$ is a benzothiazole ring which can be substituted with 1 to 4 carbon atom alkyl groups and $A_1$ is selected from the group consisting of

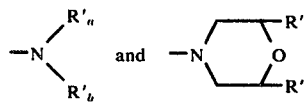

where $R'_a$ and $R'_b$ are alkyl radicals containing 1 to about 18 carbon atoms or a phenyl or cyclohexyl radical. Examples of the more preferred compounds are N,N-diethyl-2-benzothiazylsulfenamide, N,N-diisopropyl-2-benzothiazylsulfenamide, N,N-dioctyl-2-benzothiazylsulfenamide, N,N-dioctadecyl-2-benzothiazylsulfenamide, N,N-dicyclohexyl-2-benzothiazylsulfenamide, N,N-diphenyl-2-benzothiazylsulfenamide, N-oxydiethylene-2-benzothiazylsulfenamide, and the like. Excellent results are obtained when employing N-oxydiethylene-2-benzothiazylsulfenamide.

The thiazole sulfenamide accelerator is used in a level from about 1 part to about 5 parts by weight, and often from about 2 parts to 4 parts by weight per 100 parts by weight of rubber. The thiazolesulfenamide accelerator is necessary to achieve the high state of cure.

The last necessary ingredient is a morpholinothioamide compound. The compound contains the structure

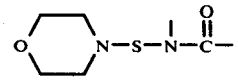

and encompasses both amides and imides. The compounds are derivatives of oxamides or cyclic hydrocarbon imides. The compounds are substituted with one or more morpholinothio groups, but usually have only one or two morpholinothio groups thereon.

The morpholinothiooxamides have the formula

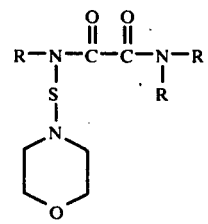

where R is defined the same as $R_a$ or is a

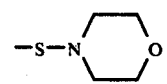

group. Designating the left hand portion of the molecule as the N,N nitrogen positions and the right hand side as the N', N' positions, examples of the compounds are: N-morpholinothio oxamide, (N,N'-dimorpholinothio) oxamide, N-morpholinothio-N',N'-diethyl oxamide, N-morpholinothio-N'-phenyl oxamide, N,N-dibenzyl-N'-morpholinothio oxamide, N-morpholinothio-N-octyl oxamide, N-morpholinothio-N-octadecyl oxamide, N-morpholinothio-N'-cyclohexyl oxamide, N-morpholinothio-N-methyl-N'-decyl oxamide, N-morpholinothio oxanilide, (N,N'-dimorpholinothio) oxanilide, and the like. If the morpholinothio oxamide contains two morpholinothio groups, preferably one group is located on each nitrogen atom; i.e., one morpholinothio group at the N position and one at the N' position.

More preferredly, the morpholinothiooxamides have the formula

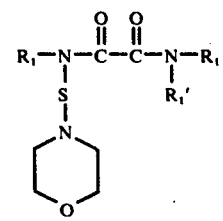

where $R_1$ is hydrogen, an alkyl radical containing 1 to about 12 carbon atoms, a phenyl radical, or a cyclohexyl radical, and $R'_1$ is the same as $R_1$ or a

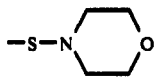

group.

Examples of the more preferred compounds are N-morpholinothiooxamide, N,N'-dimorpholinothiooxamide, N-morpholinothio-N',N'-diisopropyl oxamide, N-morpholinothio-N',N'-dicyclohexyl oxamide, N-morpholinothio-N',N'-dioctyl oxamide, N-methyl-N-morpholinothio-N',N'-diphenyl oxamide, N-morpholinothio oxanilide, N,N'-dimorpholinothio oxanilide, and the like. Excellent results are obtained when using N-morpholinothiooxamide or N-morpholinothiooxanilide.

The morpholinothioamide compounds also include morpholinothio derivatives of cyclic hydrocarbon imides. Examples of such imides are phthalimide, dihydrophthalimide, tetrahydrophthalimide, pyromellitic diimide, naphthalimides, and the like. The cyclic hydrocarbon can be further substituted with 1 to 4 carbon atom alkyl radicals. The morpholinothio cyclic hydrocarbon imides have a structure which can be represented by

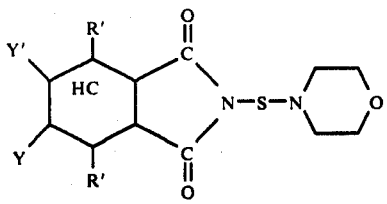

where R' is hydrogen or 1 to 4 carbon atom alkyl radicals, and Y' and Y are the same as R' or Y' and Y can form with the common carbon atoms on "HC" a cyclic hydrocarbon ring that is alicyclic or aromatic in nature or can form another cyclic imide group. Furthermore, the ring "HC" can be an aromatic or an alicyclic ring. Examples of these compounds are: when Y' and Y are equal to R', N-morpholinothiophthalimide, N-morpholinothio-dihydrophthalimide, N-morpholinothio-tetrahydrophthalimide, N-morpholinothio-5-methylphthalimide, N-morpholinothio-5,6-diethylphthalimide, and the like; when Y' and Y together with the common carbon atoms of "HC" form another cyclic imide group, N-morpholinothio pyromellitic diimide, N,N-di(morpholinothio)pyromellitic diimide, and the like; and when Y' and Y together with the commmon carbon atoms in "HC" form a cyclic hydrocarbon structure, N-morpholinothio-2,3-naphthalimide, N-morpholinothio-1,8-naphthalimide, N-morpholinothio-2,3,6,7-naphthaldiimide, and the like. Excellent results are obtained when R', Y, and Y' are hydrogen and the HC ring is aromatic or alicyclic as in N-morpholinothiophthalimide and N-morpholinothiotetrahydrophthalimide.

The morpholinothioamide compound is used in a range from about 1 to about 5 parts by weight, and more preferredly from about 1.2 parts to about 3 parts by weight based upon 100 parts by weight of rubber.

As an optional fifth ingredient, the compositions can contain either a benzothiazole accelerator or a thiuram accelerator.

The benzothiazole accelerator is a 2-thiobenzothiazole of the formula

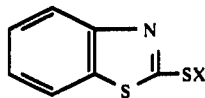

wherein X is a member selected from the group consisting of hydrogen; 1 to 18 carbon atom alkyl; aryl; halo-, nitro-, anilino- and alkyl-substituted aryl; a benzothiazolethio radical; and a mono- or divalent radical selected from the group ammonium, sodium, potassium, calcium, zinc, cadmium, copper and lead. When X is a divalent metal the second valence of the metal may be satisfied with an alkyl, aryl, substituted-aryl or preferably with a second 2-thiobenzothiazole radical. In this latter instance the compound will correspond to the structure

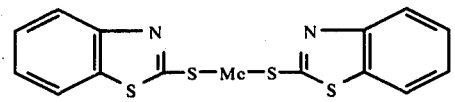

wherein Me is the divalent metal, preferably zinc, cadmium or lead. Exemplary benzothiazole compounds include: 2-mercaptobenzothiazole, 2-octylthiobenzothiazole, 2,2'-mercaptobenzothiazole disulfide, sodium 2-mercaptobenzothiazole, potassium 2-mercaptobenzothiazole, ammonium 2-mercaptobenzothiazole, zinc 2-mercaptobenzothiazole, 2-(2,4-dinitrophenylthio)-benzothiazole, and the like. Excellent results are obtained when 2-mercaptobenzothiazole or 2,2'-mercaptobenzothiazole disulfide is employed.

The level of 2-thiobenzothiazole accelerator used is from about 0.05 part to 0.5 part by weight based upon 100 parts by weight of the sulfur vulcanizable rubber. The use of this small level of 2-thiobenzothiazole accelerator yields higher original and aged stress-strain properties. If significantly higher levels of the benzothiazole accelerator are used than is taught herein scorch safety is seriously impaired.

The thiuram accelerator has the formula

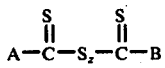

where z is 1 or 2 and A is defined as before and B is the same as A. The thiuram is used in levels from about 0.05 part to 1 part by weight based upon 100 parts by weight of the rubber, and more preferably from about 0.1 part to about 0.5 part by weight. The use of a thiuram accelerator yields higher original and aged stress-strain properties. Again, the use of levels significantly higher than those designated seriously impairs scorch safety. Examples of the thiuram sulfide compounds are tetramethylthiuram monosulfide, tetraethylthiuram monosulfide, tetrabutylthiuram monosulfide, tetramethylthiuram disulfide, tetraethylthiuram disulfide, tetrabutylthiuram disulfide, tetraoctylthiuram disulfide, tetradodecylthiuram disulfide, tetraoctadecylthiuram disulfide, tetrabenzylthiuram disulfide, tetracyclohexylthiuram disulfide, N,N-dimethyl-N', N'-dibenzylthiuram disulfide, N,N-dimethyl-N',N'-diphenylthiuram disulfide, N,N-diethyl-N',N'-didecylthiuram disulfide, N-pentamethylene-N',N'-dimethylthiuram disulfide, N,N-diethyl-N'-hexamethylenethiuram disulfide,N,N'-dipentamethylenethiuram disulfide, N-oxydiethylene-N',N'-dimethylthiuram disulfide, and the like.

More preferably, the thiuram has A and B groups which are

groups, wherein $R_a'$ and $R_b'$ are defined as before. Even more preferred thiurams are tetraalkylthiurams, examples of which include tetramethylthiuram monosulfide, tetramethylthiuram disulfide, tetraethylthiuram monosulfide, tetraethylthiuram disulfide, tetrabutylthiuram disulfide, tetrahexylthiuram disulfide, tetradecylthiuram monosulfide, and the like.

Many compounding ingredients may be used with the novel compositions. Such ingredients include activators such as zinc, calcium, and magnesium oxide, lead monoxide and dioxide, fatty acids such as stearic and lauric acid, and salts thereof such as cadmium, zinc and copper stearate and lead oleate; fillers such as channel blacks, reinforcing blacks, and thermal blacks, calcium and magnesium carbonate, calcium and barium sulfates, aluminum silicates, phenol-formaldehyde and polystyrene resins, asbestos, and the like; plasticizers and extenders such as dialkyl and diaryl organic acids like diisobutyl, diisooctyl, diisodecyl, and dibenzyl oleates, stearates, sebacates, azelates, phthalates, and the like, ASTM type 2 petroleum oils, ASTM D-2226 aromatic, naphthalenic and paraffinic oils, castor oil, tall oil, glycerin, and the like; antioxidants, antiozonants, and stabilizers such as di-β-naphthyl-p-phenylenediamine, phenyl-β-naphthylamine, dioctyl-p-phenylenediamine, N-1,3-dimethylbutyl-N-phenyl-p-phenylenediamine, 4-isopropylamino diphenylamine, 2,6-di-t-butyl paracresol, 2,2'-methylenebis-(4-ethyl-6-t-butyl phenol), 2,2'-thiobis-(4-methyl-6-t-butyl phenol), bisphenol-2,2'-methylene-bis-6-t-butyl-4-ethyl phenol, 4,4'-butylidenebis-(6-t-butyl-m-cresol), 2-(4-hydroxy-3,5-t-butylaniline)-4,6-bis(octylthio)-1,3,5-triazine, hexahydro-1,3,5-tris-β-(3,5-di-t-butyl-4-hydroxyphenyl)propionyl-s-triazine, tris-(3,5-di-t-butyl-4-hydroxybenzyl)isocyanurate, tetrakismethylene-3(3',5'-di-t-butyl-4'-hydroxyphenyl)propionate methane, distearyl thiodipropionate, dilauryl thiodipropionate, tri(nonylatedphenyl) phosphite, and the like; and other ingredients such as pigments, tackifiers, flame retardants, fungicides, and the like.

The novel compositions present a unique balancing of the influences of each ingredient, which balance is struck only in the presence of the defined morpholinothioamide compound.

The morpholinothioamides are prepared by reacting N-morpholinosulfenyl chloride with the corresponding oxamide or cyclic hydrocarbon imide. The reactants are employed on about a 1 to 1 molar ratio, though an excess of either compound, preferably the amide, can be used. A base catalyst such as a tertiary amine like trimethyl amine or triethyl amine is used. The N-morpholinosulfenyl chloride is prepared prior to use. It is usually stored as a solution of the compund in carbon tetrachloride, trichloroethylene, or the like (which also serves as a solvent for the reaction). The morpholinosulfenyl chloride must be prepared, stored, and used in the absence of water, as it reacts strongly and even violently, with water.

The oxamide employed has the formula

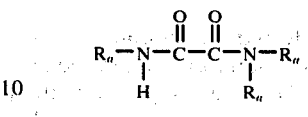

where $R_n$ is defined as above. The cyclic hydrocarbon imide employed has a labile hydrogen on the imide nitrogen atom; i.e., has a

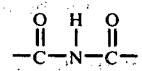

group. Examples of the oxamides and imides are oxamide, diethyloxamide, oxanilide, phthalimide, 2,3-naphthalimide, pyromellitic diimide, and the like.

The amide (or imide) is added to a reactor vessel containing a solvent therefor. Examples of solvents are tetrahydrofuran, dimethylacetamide, dimethylformamide, and the like. The base catalyst is added, followed by a solution of N-morpholinosulfenyl chloride which is added slowly to the reactor mix. The solvent for the amide and the sulfenyl chloride are usually different and may not be miscible in each other. An exothermic reaction occurs upon the addition of the morpholinosulfenyl chloride. Temperature of the reaction ranges from about 10° to about 60° C. External heating or cooling can be employed to control the temperature. Reaction time is from about 1 to 5 hours. The morpholinothioamide that forms is usually not soluble in the solvent(s), and precipitates out as it is formed thereby resulting in a slurry. After reaction, the reactor slurry is cooled down and the product filtered out. The material is dried, and can be purified by washing with water or acetone and/or by recrystallizing the material from ethanol-acetone, chloroform, carbon tetrachloride-benzene, or other solvent(s). When the amide (or imide) employed has two or more labile hydrogen atoms on it, the resulting morpholinothioamide can contain more than one morpholinothio group.

The novel vulcanizable rubber compositions described herein were evaluated for their scorch safety and their cured original and aged properties, with particular attention given to stress-strain properties; i.e., tensile, modulus, and elongation. Scorch time can be measured using a number of different methods. A standard method is ASTM procedure D-1646, wherein, using a large rotor, a $T_5$ value is determined at a specific temperature. This value is the time in minutes for a composition, heated at a given temperature, to rise 5 units over a minimum viscosity value. Scorch time can also be determined using a Monsanto Rheometer and measuring $T_2$, the time in minutes for a heated composition to register an advance of 2 chart units over the minimum value. Another method is to use the B.F.G. Cone Curometer described in U.S. Pat. No. 3,494,172, and measure $T_s$, 2 or $T_s$, 3, the time to rise 2 (or 3) inch-pounds over a minimum torque value. Original tensile, modulus, and elongation were measured following ASTM D-412. Hardness was measured following ASTM D-676 (Durometer A). Aging was done at 212° F. in an oven following ASTM D-573. Hysteresis data was obtained following the procedure ASTM D-623 (B.F.G. Flexometer).

The following Examples serve to more fully illustrate the invention.

EXAMPLE I

Preparation of 4-morpholinosulfenyl cloride.

The morpholinosulfenyl chloride must be prepared, stored and used in the absence of water, as it reacts strongly and even violently with water. The reaction consists of contacting dithiobismorpholine with chlorine gas, preferably in solution. Temperature of the reaction is from about −10° to about 50° C. N,N′-dithiobismorpholine, 47.2 grams (0.2 mole) was placed in a reactor vessel containing 400 milliliters of carbon tetrachloride. The solution was cooled to 0° C. and then chlorine gas bubbled through it at a rate of 32.6 grams per hour for 27 minutes, for a total of 14.6 grams (0.205 mole). The resulting yellow-colored solution was stored for future use.

EXAMPLE II

Preparation of N-(4-morpholinothio)phthalimide.

Phthalimide, 55.9 grams (0.38 mole) was placed in a reactor vessel containing 500 milliliters of tetrahydrofuran. 40.5 grams (0.4 mole) of triethylamine was added. The morpholinosulfenyl chloride solution, prepared in Example I and containing about 0.4 mole of the compound, was employed. The solution was added at the rate of 14 milliliters per minute to the reactor solution. During the addition, the temperature rose to about 30° C. A slurry formed. The mix was stirred for 3 hours at room temperature. The product was isolated by filtration and dried to yield 68.4 grams of material. This was dissolved in an ethanol-acetone solution and precipitated out by cooling to yield 55.7 grams of white solid having a melting point of 212° to 217° C. N-(4-morpholinothio)phthalimide having the formula $C_{12}H_{12}N_2O_3S$ has 54.5% by weight of carbon, 4.6% hydrogen, 10.6% nitrogen, and 12.1% by weight of sulfur. The values found were 54.8% carbon, 4.6% hydrogen, 10.7% nitrogen, and 12.0% by weight of sulfur.

Following the procedure given above, 3.04 moles of phthalimide was dissolved in 3.28 liters of diethylformamide. 3.1 moles of triethylamine was added. A solution of about 3 moles of morpholinosulfenyl chloride in carbon tetrachloride, prepared following Example I, was slowly added. The resultant slurry was filtered, and the product washed with ethanol and dried to yield 677 grams of material having a melting point of about 210° C. The yield, based upon the amount of phthalimide used, was 88% by weight.

EXAMPLE III

Following the procedure in Example I, a solution of N-morpholinosulfenyl chloride in trichloroethylene was prepared from 23.6 grams (0.1 mole) of N,N′-dithiobismorpholine and 7.3 grams (0.103 mole) of chlorine. The solution, which contained about 0.2 mole of the sulfenyl chloride, was slowly added to a solution of 22.8 grams (0.095 mole) of oxanilide and 20.2 grams (0.2 mole) of triethylamine in 230 milliliters of dimethylacetamide. Temperature during the addition rose from room temperature to about 46° C. After stirring for 1.5 hours the resultant slurry was filtered to isolate the product. The material was washed with water. 36.2 grams of a white solid having a melting point range of 228° to 243° C. was obtained. Analytical testing showed the product to be principally N,N′-bis(4-morpholinothio)oxanilide with small amounts of N-(4-morpholinothio)oxanilide and unreacted oxanilide.

EXAMPLE IV

Natural rubber was mixed with various rubber compounding ingredients to provide a masterbatch according to the recipe: 100 parts by weight Natural pale crepe rubber, 50 parts HAF carbon black, 5 parts zinc oxide, 3 parts stearic acid, 2 parts N-1,3-dimethylbutyl-N′-phenyl-p-phenylenediamine, 0.75 part Agerite Superflex (diphenylamine-acetone condensation product), and 0.25 part N,N′-diphenyl-p-phenylenediamine. The masterbatch was mixed in a Banbury mixer following a standard mixing procedure. Portions of the masterbatch were put on a two-roll mill, and curative ingredients were added. The following recipes were evaluated (in parts by weight):

|  | 1[a] | 2 | 3 | 4 | 5 |
|---|---|---|---|---|---|
| Masterbatch | 161 | 161 | 161 | 161 | 161 |
| BMD[1] | 3.0 | — | — | — | — |
| OBTS[2] | — | 3.0 | 3.0 | 3.0 | 3.0 |
| MBT[3] | — | — | 0.1 | 0.25 | 0.38 |
| MTP[4] | — | 2.80 | 2.80 | 2.80 | 2.80 |
| Sulfur | 0.50 | 0.50 | 0.50 | 0.50 | 0.50 |
| BFG Cone Curometer data applied pressure in.-lbs./min. | 3 | 2 | 2 | 3 | 3 |
| Δtorque, inch-pounds | 88 | 107 | 111 | 79 | 80 |
| $T_s 2$, minutes | 4.4 | 10.8 | 10.5 | 7.4 | 6.6 |
| Percent increase in scorch safety | — | 146 | 138 | 68 | 50 |
| Cured 75 minutes at 284° F. |  |  |  |  |  |
| 300% modulus, psi | 2280 | 2310 | 2390 | 2210 | 2210 |
| Tensile, psi | 3930 | 3690 | 3820 | 4080 | 3990 |
| Elongation, percent | 460 | 430 | 440 | 500 | 490 |
| 6 days at 212° F. |  |  |  |  |  |
| 300% modulus, psi | — | — | 2670 | 2490 | 2500 |
| Tensile, psi | 2740 | 2500 | 2800 | 2800 | 3000 |
| Elongation, percent | 310 | 310 | 320 | 340 | 350 |
| Percent decrease in tensile | 30 | 32 | 27 | 31 | 25 |

[1]2-benzothiazyl 4-morpholino disulfide
[2]N-oxydiethylene-2-benzothiazyl sulfenamide
[3]2-mercaptobenzothiazole
[4]4-morpholinothiophthalimide from Example II
[a]average of two samples Sample 1 is a control sample. It demonstrates the short scorch time and excellent original and thermal aged properties that are obtained using a BMD-sulfur cure system. Samples 2 to 5 are novel compositions of this invention. The samples show a unique combination of improved scorch safety and excellent original and aged properties. The retention of tensile strength after aging is as good as or better than that of Sample 1, the control, while at least a 50% increase in scorch safety of a 2-thiobenzothiazole accelerator yields somewhat higher original and aged tensile properties.

EXAMPLE V

A masterbatch was prepared containing 70 parts by weight of natural rubber, 30 parts of cis-polyisoprene rubber, 50 parts of HAF carbon black, 50 parts of zinc oxide, 3.0 parts of stearic acid, 2.0 parts of N-1,3-dimethylbutyl-N'-phenyl-p-phenylenediamine, and 1.0 part of Agerite Superflex (diphenylamine-acetone condensation product). The masterbatch was used in an evaluation of various cure systems. The recipes used and data obtained are as follows:

The example demonstrates that the novel cure systems and compositions of this invention (Samples 2 to 6) exhibit as good as or better thermal aged properties as the known cure system of BMD-sulfur (Sample 1). The excellent original and aged properties are obtained along with an increase in scorch safety. Samples 3 to 6 show the use of a thiuram accelerator as an optional fifth ingredient in the compositions.

EXAMPLE VI

The masterbatch prepared in Example V was also used in an evaluation of a novel cure system using the N,N'-bis(4-morpholinothio)oxanilide prepared in Example III. The recipes used are as follows:

|  | 1[a] | 2 | 3 | 4 |
|---|---|---|---|---|
| Masterbatch | 161 | 161 | 161 | 161 |
| BMD | 3.25 | — | — | — |
| OBTS | — | 3.0 | 2.88 | 2.88 |
| MBT | — | 0.25 | 0.25 | — |
| MBTS[1] | — | — | — | 0.25 |
| BMTO[2] | — | 2.80 | 2.73 | 2.73 |
| Sulfur | 0.5 | 0.5 | 0.5 | 0.5 |
| BFG Cone Curometer applied pressure, in-lbs/min. | 3 | 3 | 3 | 3 |
| Δtorque, inch-pounds | 101 | 89 | 87 | 93 |
| T$_s$2, minutes | 7.3 | 10.8 | 17.4 | 20.7 |
| Percent increase in scorch safety | — | 48 | 138 | 184 |
| Cured 75 minutes at 284° F. | | | | |
| 300% modulus, psi | 2470 | 2420 | 2470 | 2490 |
| Tensile, psi | 3780 | 3550 | 3360 | 3390 |
| Elongation, percent | 410 | 400 | 380 | 390 |
| Aged 7 days at 212° F. | | | | |
| 300% modulus, psi | — | 2580 | — | — |
| Tensile, psi | 2600 | 2690 | 2420 | 2270 |
| Elongation, percent | 280 | 310 | 270 | 260 |
| Percent decrease in tensile | 31 | 24 | 28 | 33 |
| Percent decrease in elongation | 32 | 23 | 29 | 33 |

[1]2,2'-benzothiazyl disulfide
[2]N,N'-bis(4-morpholinothio)oxanilide
[a]average of two samples Samples 2 to 4 are novel compositions of this invention. The data shows that these compositions yield as good as or better aging properties with at least about a 50% increase in scorch safety compared to the known BMD-sulfur cure system (Sample 1).

The use of the BMD-sulfur cure system yields vulcanizates having excellent original and thermal aged properties, especially tensile, modulus, and elongation.

|  | 1[a] | 2 | 3 | 4 | 5 | 6 |
|---|---|---|---|---|---|---|
| Masterbatch | 161 | 161 | 161 | 161 | 161 | 161 |
| BMD | 3.0 | — | — | — | — | — |
| OBTS | — | 3.0 | 2.0 | 2.25 | 2.25 | 1.50 |
| MBT | — | 0.25 | — | — | — | — |
| TMTM[1] | — | — | 0.25 | 0.38 | 0.25 | 0.3 |
| MTP | — | 2.80 | 2.00 | 1.50 | 1.50 | 1.50 |
| Sulfur | 0.5 | 0.5 | 0.65 | 0.5 | 0.8 | 0.8 |
| BFG Cone Curometer applied pressure, in-lbs/min. | 3 | 3 | 4 | 4 | 3 | 3 |
| Δtorque, inch-pounds | 71 | 89 | 113 | 72 | 109 | 103 |
| T$_s$2, minutes | 6.6 | 11.0 | 9.0 | 13.4 | 9.8 | 9.2 |
| Percent increase in scorch safety | — | 67 | 36 | 103 | 49 | 39 |
| Cured 75 minutes at 284° F. | | | | | | |
| 300% modulus, psi | 2230 | 2280 | 2570 | 2310 | 2690 | 2660 |
| Tensile, psi | 3950 | 3350 | 4010 | 3590 | 3440 | 3610 |
| Elongation, percent | 460 | 400 | 430 | 420 | 360 | 380 |
| Aged 7 days at 212° F. | | | | | | |
| 300% modulus, psi | — | 2610 | 2610 | 2520 | — | — |
| Tensile, psi | 2660 | 2680 | 2830 | 2720 | 2230 | 2570 |
| Elongation, percent | 300 | 310 | 320 | 320 | 240 | 290 |
| Percent decrease in tensile | 33 | 20 | 29 | 24 | 35 | 29 |
| Percent decrease in elongation | 35 | 23 | 26 | 24 | 33 | 24 |

[1]tetramethylthiuram monosulfide
[a]average of two samples

Such vulcanizates would be particularly useful as hose, molded gaskets, tires and the like which are subject to heat during their use. The BMD-sulfur cure system is limited in its use by its relatively short scorch time. The use of known cure retarders and vulcanization inhibitors does not provide for significantly increased scorch time. For example, Santogard PVI (N-cyclohexylthiophthalimide) a commercial cure retarder, was used at 1.0 part per 100 parts of rubber in the masterbatch recipe given in Example IV. 3 parts of BMD and 0.5 part of sulfur was used as the cure system. BFG Cone Curometer data was obtained at 284° F. $T_s$, 2 of the recipe without the Santogard PVI present was 3.9 minutes. With 1.0 part of PVI present, the $T_s$, 2 value was 4.8 minutes, an increase in scorch safety of only 23%. At no time, in the experiments run, did the PVI increase scorch safety over 50% of the control value. In contrast, many times the novel cure systems of this invention increased scorch safety, at no loss in aging characteristics, over 50% and up to about 20%.

Following the procedures given in Examples I, II and III, other morpholinothioamide compounds were prepared. Morpholinosulfenyl chloride was reacted with 2-imidazolidinone to prepare both 1,3-bis(4-morpholinothio)-2-imidazolidinone and the mono-substituted compound. Other compounds prepared were N-(4-morpholinothio)succinimide, N-(4-morpholinothio)-0-ben-zoic sulfimide, N-(4-morpholinothio)-hydantoin, and N,N'-bis(4-morpholinothio)hydantoin. All six of the compounds were evaluated for their utility in the compositions disclosed in this application. None of these compounds yielded a composition having both the increased scorch safety and the excellent original and aged properties of the claimed compositions. This illustrates the unique features of the claimed morpholinothio-oxamides and morpholinothio cyclic imides.

I claim:

1. A morpholinothiooxamide of the formula

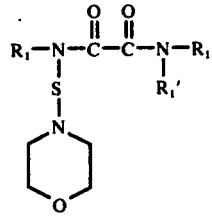

wherein $R_1$ is selected from the group consisting of hydrogen, alkyl radicals containing 1 to about 12 carbon atoms, a phenyl radical, and a cyclohexyl radical, and $R_1'$ is the same as $R_1$ or is the group

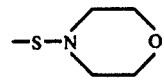

2. A compound of claim 1, N,N'-bis(4-morpholinothio)oxanilide.

3. A compound of claim 1, N,N'-bis(4-morpholinothio)-oxamide.

* * * * *